United States Patent [19]

Pham et al.

[11] Patent Number: 5,275,058
[45] Date of Patent: Jan. 4, 1994

[54] METHOD AND APPARATUS FOR DETECTING WIRE BOND PULL TEST FAILURE MODES

[75] Inventors: Cuong V. Pham, Livonia; Brian J. Hayden, Royal Oak, both of Mich.

[73] Assignee: Ford Motor Company, Dearborn, Mich.

[21] Appl. No.: 968,938

[22] Filed: Oct. 30, 1992

[51] Int. Cl.⁵ ............................................. G01N 3/08
[52] U.S. Cl. ....................................... 73/827; 324/538
[58] Field of Search .................. 73/827; 324/538, 555

[56] References Cited

U.S. PATENT DOCUMENTS

| | | | |
|---|---|---|---|
| 3,564,911 | 2/1971 | Slemmons et al. | 73/95 |
| 3,572,108 | 3/1971 | McShane et al. | 73/95 |
| 3,945,248 | 3/1976 | West | 73/88 |
| 4,282,759 | 8/1981 | Merrell | 73/827 |
| 4,453,414 | 6/1984 | Ronemus et al. | 73/827 |
| 4,697,461 | 10/1987 | Jabs | 73/862.53 |
| 4,895,028 | 1/1990 | Mayer | 73/827 |
| 4,907,458 | 3/1990 | Biggs et al. | 73/827 |
| 5,214,963 | 6/1993 | Widder | 73/827 |

*Primary Examiner*—Jerry W. Myracle
*Attorney, Agent, or Firm*—Roger L. May; Paul K. Godwin, Jr.

[57] ABSTRACT

Provided is a method and apparatus for electrically detecting the location of bond failure and wire breakage occurring during tensile strength testing of a wire sample having first and second bond foots affixed to respective first and second support pads. The method and apparatus monitors the voltage levels of first and second electrically conductive probes. The first probe has a primary lead in electrical contact with the first support pad and a secondary lead in electrical contact with the first bond foot. Similarly, the second electrically conductive probe has a primary lead in electrical contact with the second support pad and a secondary lead in electrical contact with the second bond foot. Voltage detection circuitry is provided in electrical contact with the first and second probes for detecting the voltage level at each of the respective primary and secondary leads to generate the respective corresponding output signals. Comparator circuitry is further provided in electrical contact with the voltage detection circuitry for receiving and comparing each of the output signals to a selected reference value and generating a supplemental output signal indicating the location of bond failure or wire breakage.

14 Claims, 8 Drawing Sheets

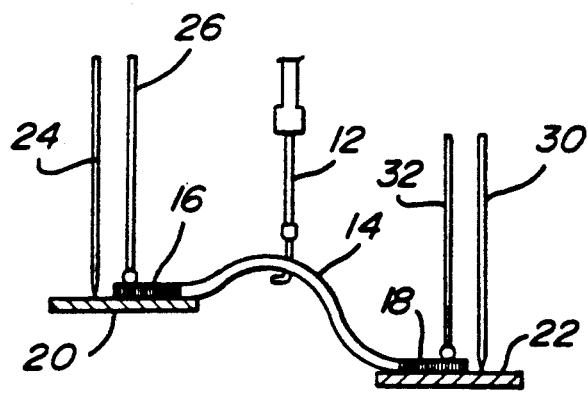
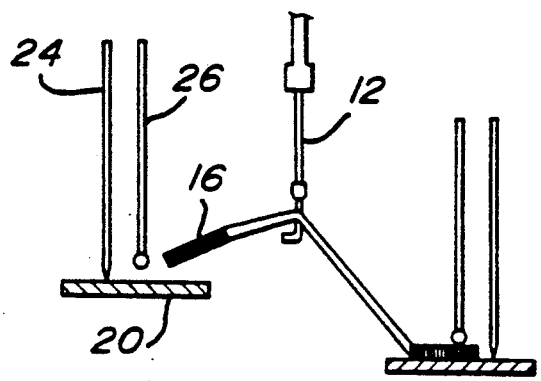
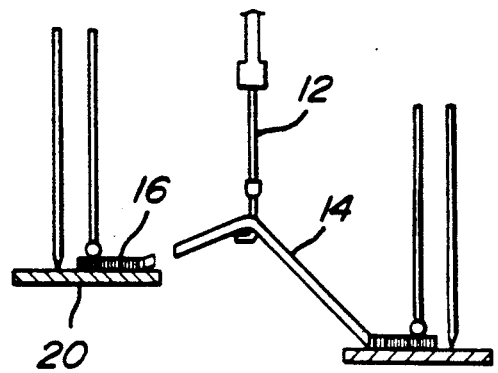

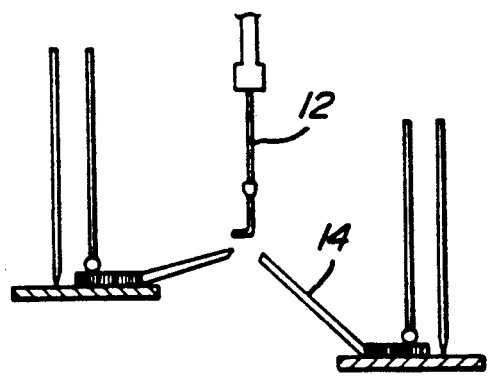
fig-3d
fig-3e
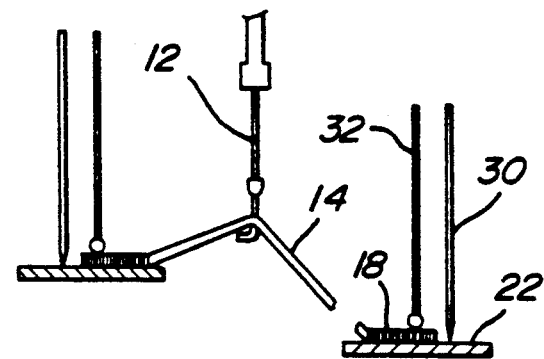
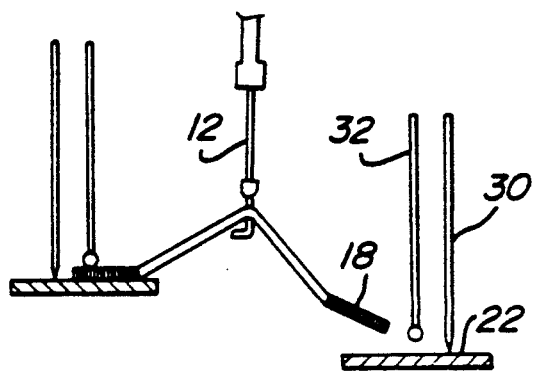
fig-3f

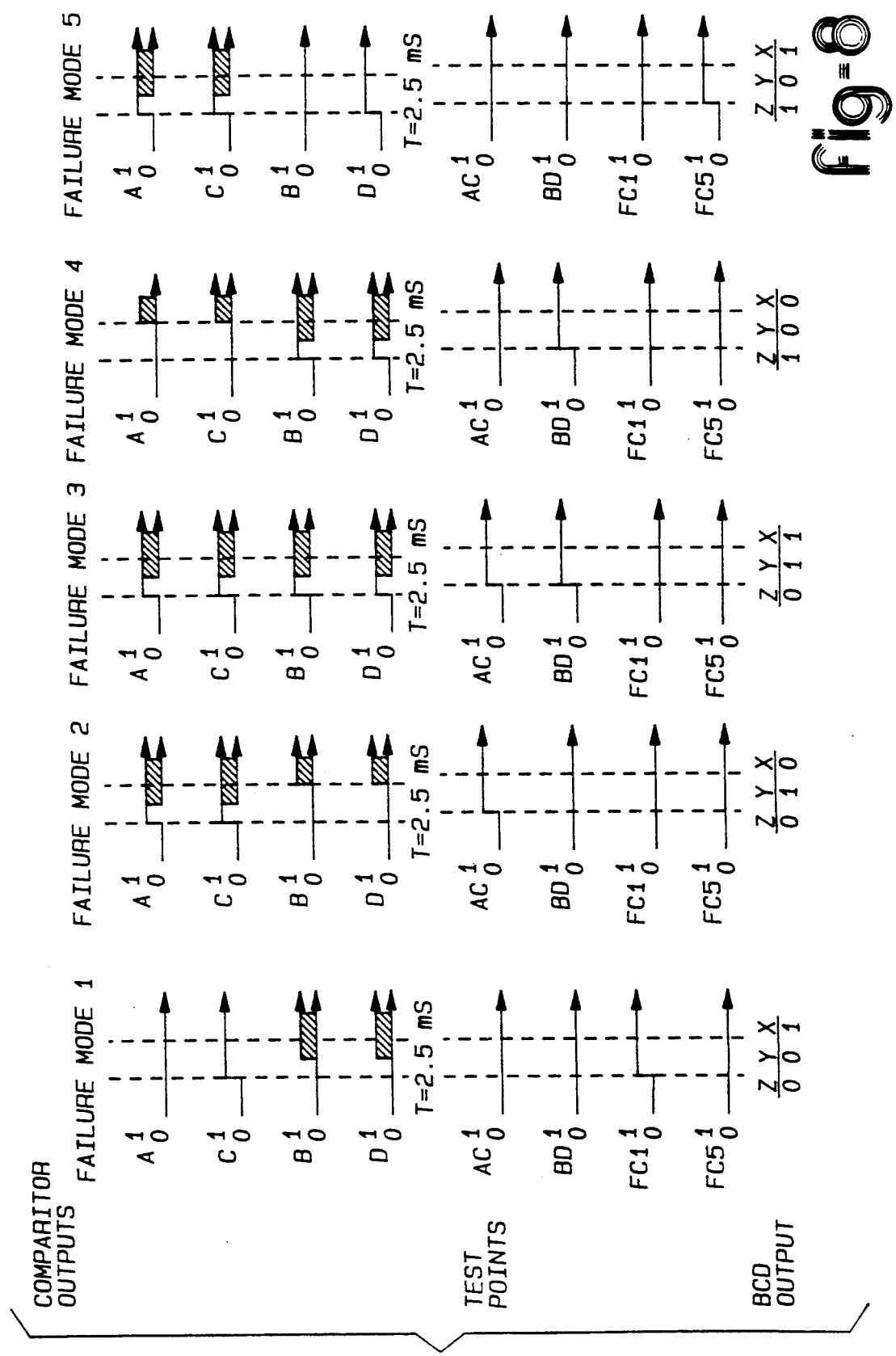

METHOD AND APPARATUS FOR DETECTING WIRE BOND PULL TEST FAILURE MODES

TECHNICAL FIELD

The present invention relates generally to wire bond pull testing, and more particularly to a method and apparatus for electrically detecting the location of bond failure and wire breakage occurring during tensile strength testing.

BACKGROUND ART

As electronic technology advances, larger numbers of electronic components may be formed and interconnected as integrated circuitry on common substrates. Separate wire interconnections are still required, however, to connect integrated circuit chips to non-integrated circuit components and to other integrated circuits as well as connector leads and pins. These interconnections are typically accomplished by bonding one end of a selected interconnect wire to a first circuit point with the aid of a bonding tool. Thereafter, the length of the interconnect wire is then paid out to form a loop between the first circuit point and a selected second circuit point. The wire is then bonded to the second circuit point and the standing part of the wire is broken adjacent to the second circuit point.

Historically, this bonding has been accomplished by placing the end of a bonding tool against the upper surface of the wire and applying pressure to hold the lower surface of the wire against the circuit point to which the wire is to be bonded. Sonic energy is imparted to the wire and the circuit point at the end of the bonding tool to cause mechanical and electrical bonding of the wire and circuit point.

Regardless of the bonding technique utilized, those skilled in the art will recognize that the reliability of the related microelectronic systems is directly related to the tensile strength of the interconnect wires referenced above and the reliability of the bonds created at the first and second circuit points. Various methods and apparatus have thus been designed and used to determine the tensile strength of interconnect wires for research purposes as well as quality control measures during conventional production processes.

See, for example, U.S. Pat. No. 3,564,911 issued to J. W. Slemmons et al. which discloses a wire bond strength tester comprising a self-centering and self-damping hook which is suspended from one end of a balanced beam disposed for pivoting about a pivot point between the extremities. The beam is loaded with a weight as a function of a required pulling force to be applied by the hook assembly. In operation, a test circuit is moved under the hook and the beam is tilted to permit the hook to engage an interconnect wire of a microelectronic circuit. In operation, a wire is engaged and the beam is thereafter permitted to pivot upwards in response to the applied load. An upper mechanical stop is also provided to prevent excessive pivoting and to test the vertical slack of the conductor. If the bond of the interconnect wire or its vertical slack is within the required limits, the upper mechanical stop is not contacted and a successful test is indicated. In contrast, if a mechanical stop is contacted, an unsuccessful test is indicated.

U.S. Pat. No. 4,282,759 issued to Merrell discloses a method and apparatus for non-destructive testing of beam-lead integrated circuit connections. As disclosed by Merrell, a beam-leaded device is provided in which each individual lead has pull tab with a weakened area thereon in order to provide a non-destructive means for testing the beam leads. The beam-lead device is tested by inserting a hook of a gram pull tester into an opening at the tab and pulling on the tab until the weakened area is broken. The weakened area is selected such that it will break when subjected to a predetermined pull. This predetermined amount is selected to be less than that required to break the tensile strength of the diffusion bond between the beam-leads and the conductors to which they are connected.

U.S. Pat. No. 4,697,461 issued to Jabs discloses a method and apparatus for verifying the seismic integrity of an electronic component. According to the invention, a force of a desired magnitude is applied to the lead of an electronic component contained in an electric circuit. The magnitude of the force corresponds to the expected maximum force which would be exerted on the lead by an earthquake. An indication is thus provided when the lead has been subjected to the applied force for a given period of time corresponding to the approximate period of time the maximum force of an earthquake would be exerted on the lead. This force is released if the desired magnitude has been applied for a further preset period of time which is greater than the given period of time, or if the magnitude of the applied force exceeds a preset maximum value.

U.S. Pat. No. 4,453,414 issued to Ronemus et al. discloses a method of testing the bond strength between a lead and an electrical device which includes mounting the device to a pedestal which is coupled to a load sensor. As disclosed by Ronemus, the lead is pulled from the device by a freely manipulatable grasping tool. A load differential indicated by the load sensor is observed as an indication of the bond strength between the lead and the device. The apparatus in accordance with the invention includes a support arm which is movable along a predetermined path and to which is mounted a pedestal for supporting a device, the leads of which are to be pull tested. A predetermined bias force resists a movement of the arms such that a movement of the arm registers a predetermined minimal pull strength of the leads.

U.S. Pat. No. 4,907,458 issued Biggs et al. discloses a method and apparatus for testing microcircuitry bonds. According to the invention, a wire bond is engaged by a hook, and the force with which that wire is urged to move away from the hook is measured as the force required to maintain the hook stationary. In the preferred method, the hook is fixed to a structure whose vertical position remains substantially fixed while the magnitude of the pulling force is measured. The vertical position of the electronic apparatus remains fixed while the hook is moved vertically and rotationally to place the hook under a wire notwithstanding that such a method requires capability of vertical movement of both the electronic apparatus and the hook.

U.S. Pat. No. 4,895,028 issued to Mayer discloses a method of pull-testing wire connectors on an electrical device. According to the invention, an upward pulling force is applied to a wire loop by a motor-driven loading arm through a hook which is connected to the free end of a flexible cantilever beam in the arm. A strain gauge is provided in the beam to measure its deflection and thus the applied pulling force and supply a signal corresponding to this measured force. The actual force is applied to the bonds and is calculated by generating a signal signifying the distance the hook has moved when the strain gauge starts to generate a signal.

The conventional prior art devices discussed above provide a general background in respect of the design and use of pull testing methods and apparatus for determining bond and tensile strength. For the most part, these device have been used in connection with conventional manufacturing processes to ensure the reliability of the selected bonds and interconnect wires.

While the prior art systems provide a broad indication of tensile strength, they do not provide any indication of the specific failure mode, i.e. whether there has been a break at the center span, upper bond, lower bond, or a lift of the respective bonds. From a research standpoint, this information is of critical importance to provide meaningful feedback for the selection of future interconnect wires having varying diameters, length and bonds. At present, technicians must visually inspect such failure modes and record the resultant information on an individual basis. As readily seen, this approach requires substantial labor and resultant costs which inevitably must be passed on to the consumer.

SUMMARY OF THE INVENTION

It is an object of the present invention to overcome the problems of the prior art systems by providing a method and apparatus for electrically detecting the location of bond failure and wire breakage occurring tensile strength testing of an interconnect wire sample. As disclosed herein, the present invention significantly reduces time and labor required by technicians to perform and record their testing and thus avoid substantial labor costs associated with the prior art systems and methods. Because the results of each testing operation are calculated, recorded and stored, through use of a corresponding computer, the method and apparatus of the present invention also obviates the adverse results of human errors which are inherent in the prior art systems.

In carrying out the above object, the apparatus of the present invention comprises a first electrically conductive probe having a primary lead in electrical contact with a first support pad and a secondary lead in electrical contact with a first bond foot. A secondary electrical conductive probe is also provided having a primary lead in electrical contact with a second support pad and a secondary lead in electrical contact with a second bond foot. Voltage detection means is also provided in electrical contact with the first and second probes for detecting the voltage level at each of the respective primary and secondary leads and to generate respective output signals corresponding thereto. There is further provided a comparator means in electrical contact with the voltage detection means for receiving the output signals from the first and second electrically conductive probes and for comparing each of the signals to a selected reference value. Based upon this comparison, a supplemental output signal is generated indicating the location of bond failure or wire breakage.

Attention is further directed to Applicants' method for electrically detecting the location of bond failure and wire breakage which includes the provision of first and second electrically conductive probes, each having a primary lead in electrical contact with a corresponding support pad and a secondary lead in electrical contact with a corresponding bond foot. In operation, a selected electrical potential is applied to each of the secondary leads and the voltage at each of the primary and secondary leads is thereafter detected. A plurality of output signals are generated, each corresponding to one of the detected voltages. The output signals are compared to a selected reference value and a first plurality of binary output signals are generated. Each of these output signals indicate whether the detected voltages exceeds the selected reference value. A second plurality of binary output signals is thereafter generated, each of which corresponds to the product of selected binary input signals.

A third plurality of binary output signals are also generated, each of which correspond to the sum of selected binary input signals. Finally, a forth plurality of binary output signals are generated which correspond to and indicate the detected bond failure or wire breakage.

Accordingly, a general object of the present invention is the provision of an apparatus for electrically detecting the location of bond failure and wire breakage occurring during tensile strength testing of a wire sample having first and second bond foots affixed to respective first and second support pads.

Another object of the present invention is the provision of a method for electrically detecting the location of bond failure and wire breakage occurring during tensile strength testing.

A more specific object of the present invention is the provision of a method for electrically detecting the location of bond failure and wire breakage occurring during tensile strength testing of a wire sample having first and second bond foots affixed to respective first and second support pads and generating a plurality of binary output signals corresponding to the detected failure.

The above objects and other objects, features, and advantages of the present invention are readily apparent from the following detailed description of the best modes for carrying out the invention when taken in connection with the accompanying drawings.

BRIEF DESCRIPTION OF THE DRAWINGS

FIGS. 3A-3F are schematic diagrams of the apparatus of the present invention shown with the interconnect wire and bond foots in various failure modes;

FIG. 8 is a logic diagram illustrating the various failure modes anticipated by the present invention and a corresponding logic output of the circuit components.

BEST MODE FOR CARRYING OUT THE INVENTION

Figure 1:
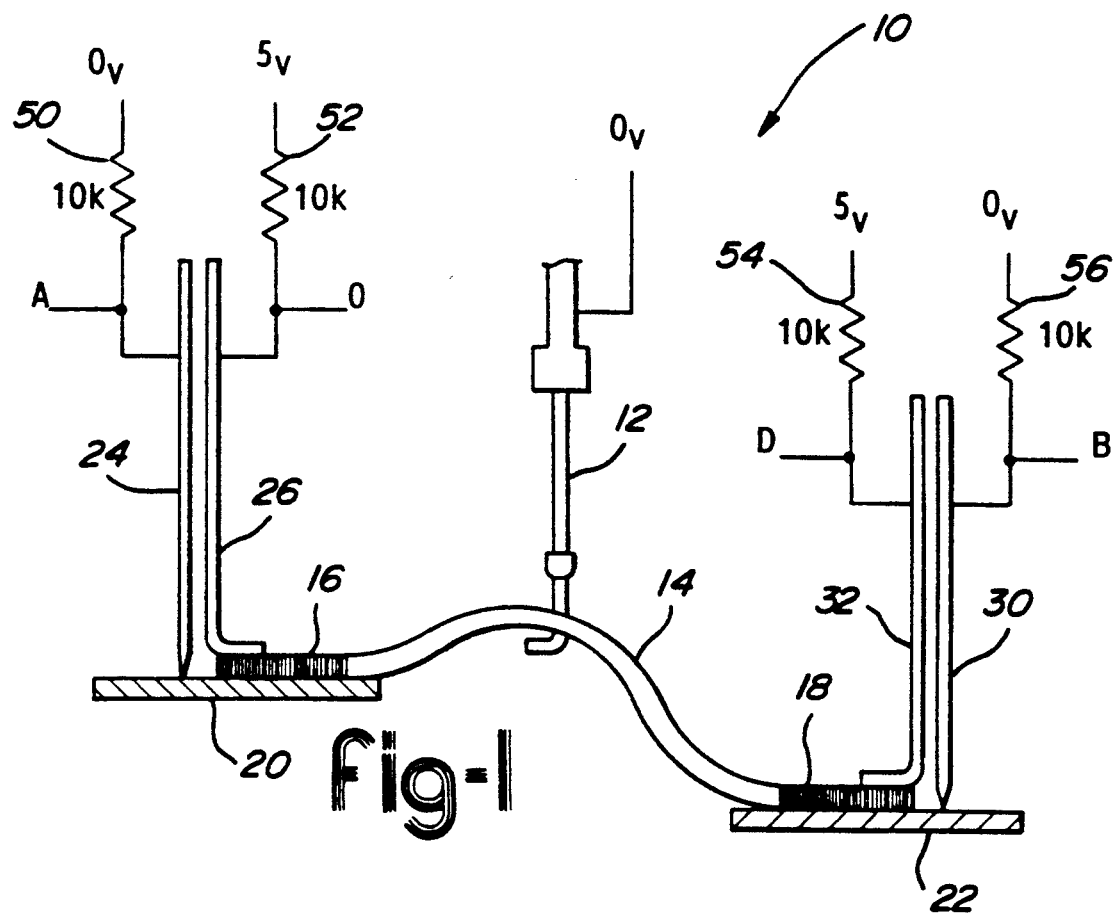
FIG. 1 is a schematic diagram of a wire bond pull testing apparatus according to the present invention.
Figure 2:
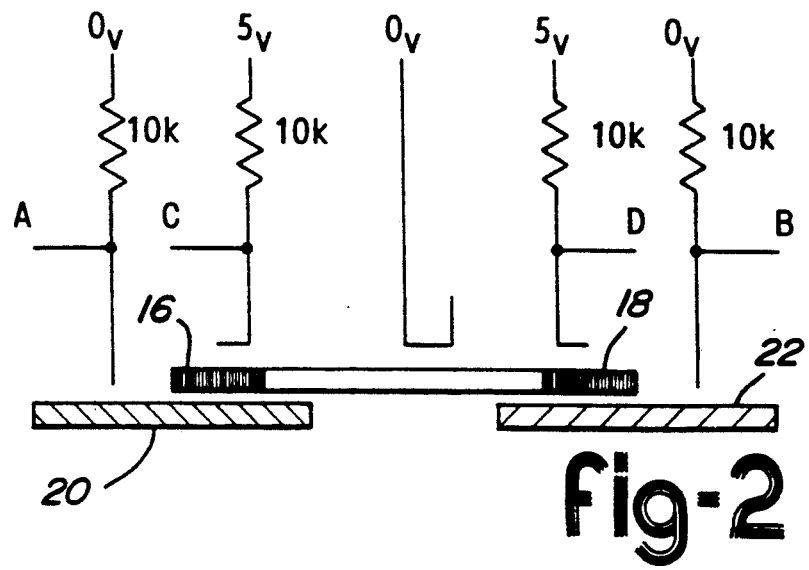
FIG. 2 is a schematic circuit diagram of the apparatus of the present invention as shown in FIG. 1.
Figure 4:
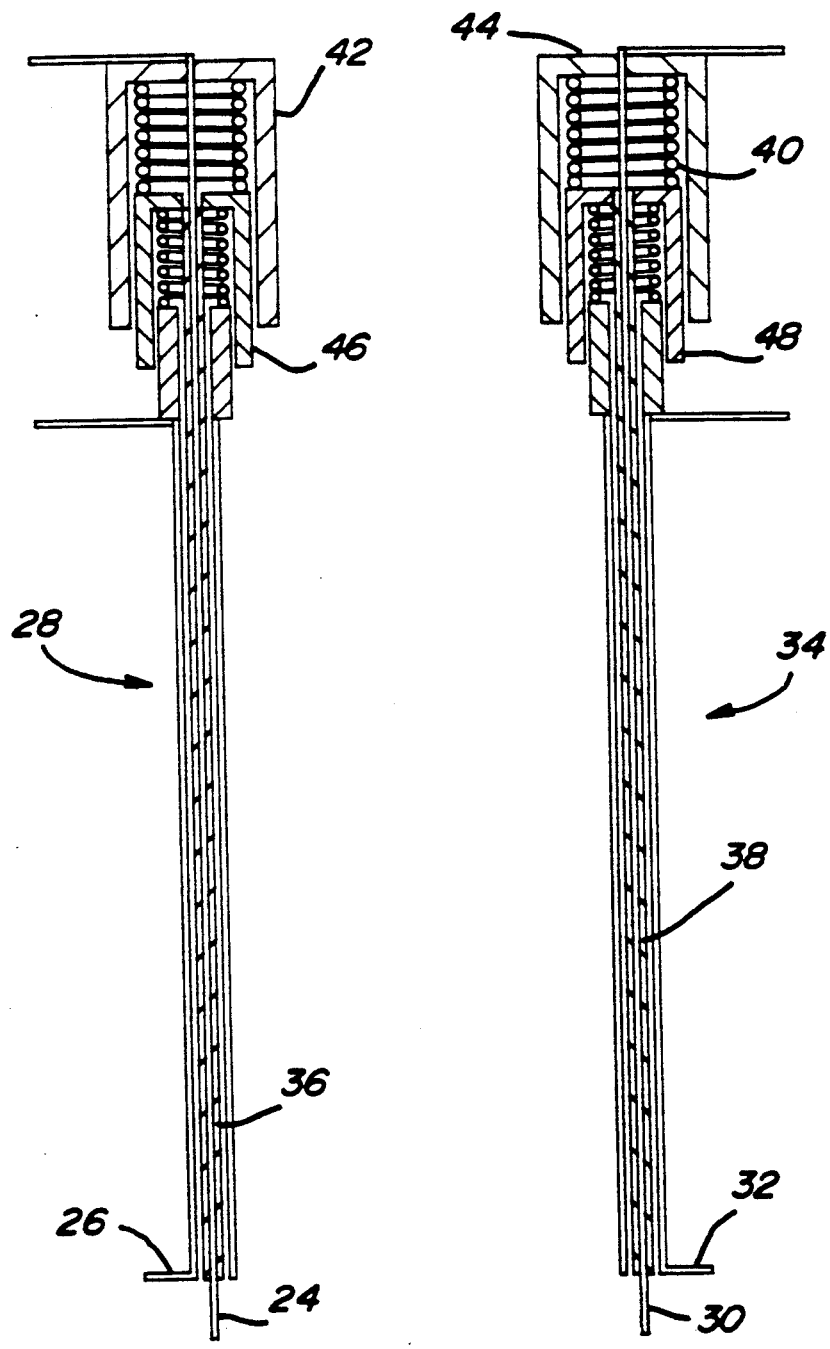
FIG. 4 is a cross-sectional view of the first and second electrically conductive probes of the present invention as shown in FIGS. 1-3.

With reference to FIGS. 1 and 4 of the drawings, there is shown a schematic diagram of the apparatus of the present invention indicated generally by reference numeral 10. Apparatus 10 includes a test hook 12 extending from a pull test machine of the type such as Series 25 Microtester, manufactured by Dage Precision Industries, Inc. of Freemont, Calif. Test hook 12 is shown in electrical and physical contact with interconnect wire 14 which has first and second bond foots 16 and 18 affixed to respective first and second support pads 20 and 22. Also shown in FIG. 1 are primary and secondary leads 24 and 26 which extend from a first electrically conductive probe generally designated by reference numeral 28 in FIG. 4. Similarly, primary and secondary leads 30 and 32 are shown in FIG. 1 which extend from a second electrically conductive probe 34, also shown more thoroughly in FIG. 4.

Still referring to FIG. 1, it is seen that primary lead 24 of the first electrically conductive probe 28 is in electrical and mechanical contact with first bond foot 20. Similarly, primary lead 30 of the second electrically conductive probe 34 is in electrical and mechanical contact with second support pad 22. The respective secondary leads 26 and 32 of the respective first and second electrically conductive probes 28 and 34 are also in electrical and mechanical contact with respective first and second bond foots 16 and 18.

Figure 5:
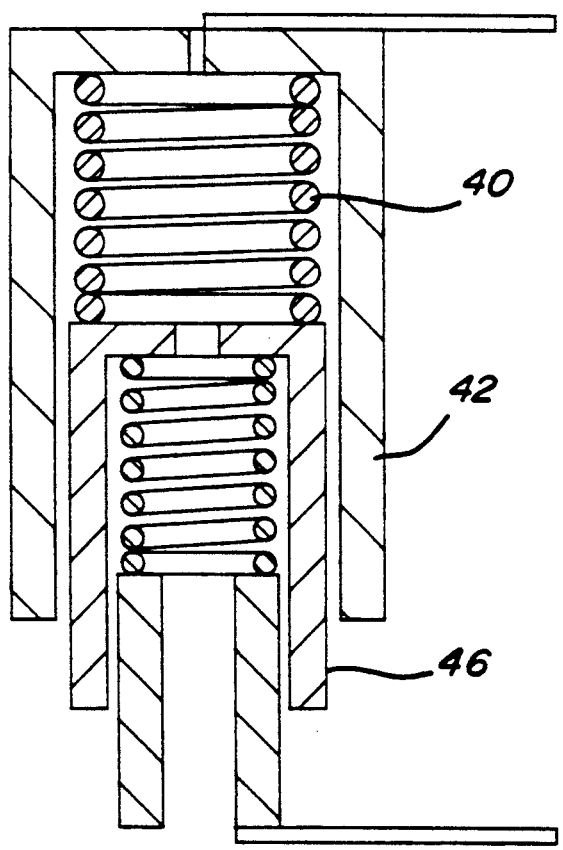
FIG. 5 is an exploded cross-sectional view of an electrically conductive probe according to the present invention illustrating the interconnection between the primary and secondary leads.

With reference to FIGS. 4-5, the relationship between the primary and secondary leads of the respective first and second electrically conductive probes 28 and 34 will be described in more detail. As seen in FIG. 4, each of the electrically conductive probes 28 and 34 include respective primary leads 24 and 30 and secondary leads 26 and 32. Primary leads 24 and 30 are electrically isolated from secondary leads 26 and 32 by insulation means 36 and 38. In the preferred embodiment, the respective primary and secondary leads of the first and second electrically conductive probes are spring-loaded and independently movable with respect to one another. Springs 40 are more specifically identified in FIG. 5. The first and second electrically conductive probes 28 and 34 are shown in the preferred embodiment as having a dual spring arrangement with respective primary insulating caps 42 and 44 and secondary insulating caps 46 and 48.

With reference now to FIGS. 1-5, there is seen that in the preferred embodiment test hook 12 is grounded, thus having a 0 voltage potential impressed thereon at the center span 13 of interconnect wire 14. The electrical circuit according to the present invention is provided input from the first and second electrically conductive probes 28 and 34 and their respective primary and secondary leads 24, 32, 26 and 30 as shown in FIG. 1 at references A, B, C and D. In the preferred embodiment, a five volt potential is also impressed on secondary leads 26 and 32.

Figure 7:
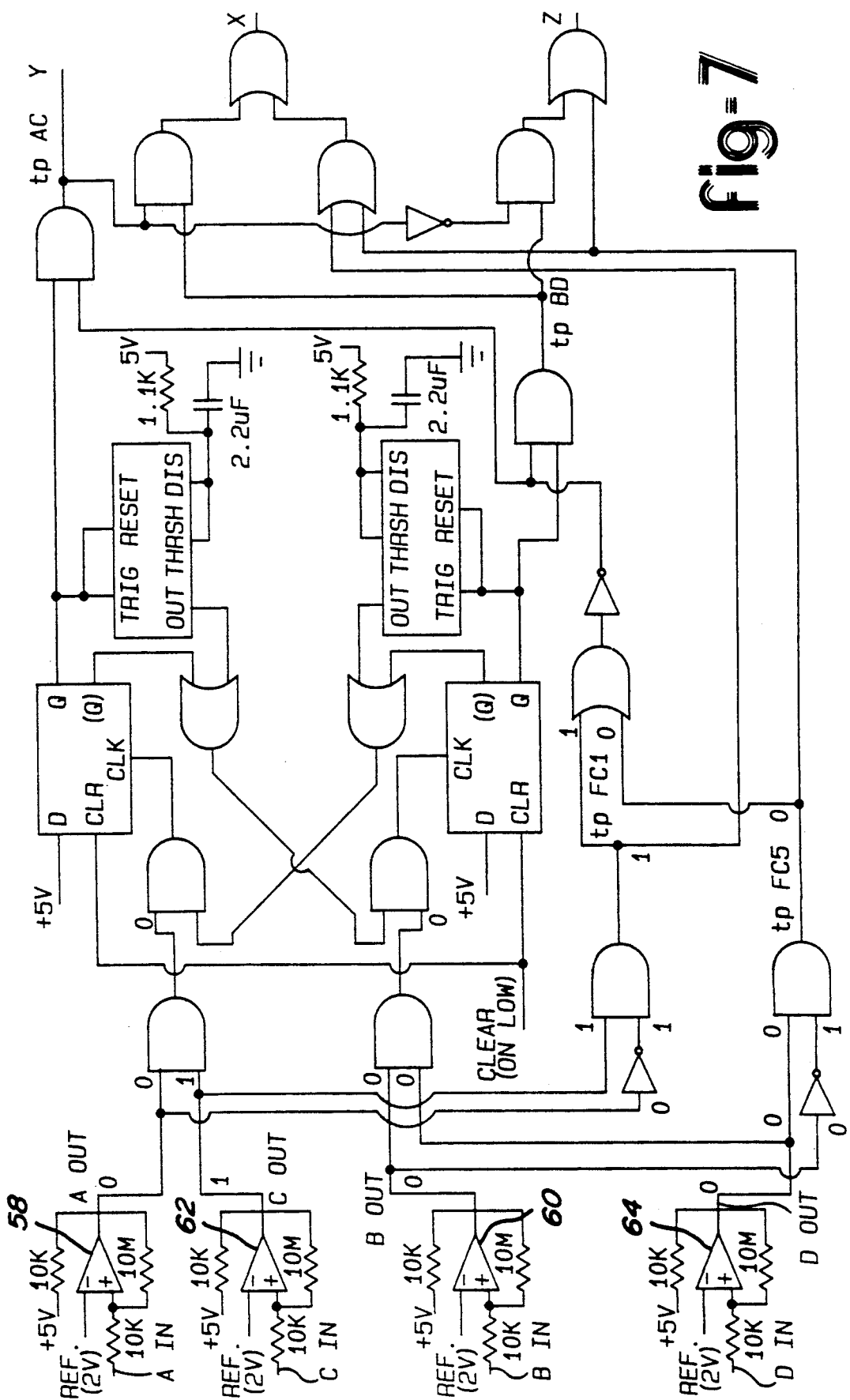
FIG. 7 is a detailed schematic circuit diagram of the wire bond pull test failure mode detection circuit as shown in FIG. 6.

Turning for the moment to FIGS. 7 and 8, a control circuit in accordance with the present invention is shown in further detail for receiving input from the primary and secondary leads of the first and second electrically conductive probes 28 and 34. Those skilled in the art will recognize from an overview of the circuit provided in FIGS. 7 and 8 that digital components have been utilized by Applicants to provide a binary-coded decimal output indicative of the specific failure mode resulting from each selected pull test. The operation of the circuit will be described in further detail below.

The specific failure modes sought to be identified and recorded by the present invention are shown in more detail in FIGS. 3A-3F. As shown in FIG. 3A, first and second bond foots 16 and 18 of interconnect wire 14 are bonded to first and second support pads 20 and 22, respectively. No wire breakage or bond failure is shown.

Turning now to FIG. 3B, however, attention is directed to first bond foot 16 which is shown lifted from first support pad 20 and secondary lead 26. Similarly, FIG. 3C illustrates a break at the heel of interconnect wire 14 above bond foot 16. FIG. 3D shows a break at the center span of interconnect wire 14 while FIG. 3E illustrates a break at the heel of interconnect wire 14 above bond foot 18. Finally, FIG. 3F illustrates a lift at bond foot 18 from support pad 22 and secondary lead 32.

OPERATION

Initial State

With reference to FIGS. 1-3 and 7-8, the operation of the apparatus of the present invention will be described in further detail. As indicated above, the general object of the present invention is to detect voltage levels at the primary and secondary leads of first and second probes 28 and 34 and process information to provide a binary coded decimal output corresponding to the electrically detected failure mode. By way of example, FIG. 3A illustrates the initial state where no wire or bond breakage has occurred. In this state, grounded test hook 12 creates a shorted circuit at reference points A-D, thus the corresponding detected voltages are all 0.

Figure 6:
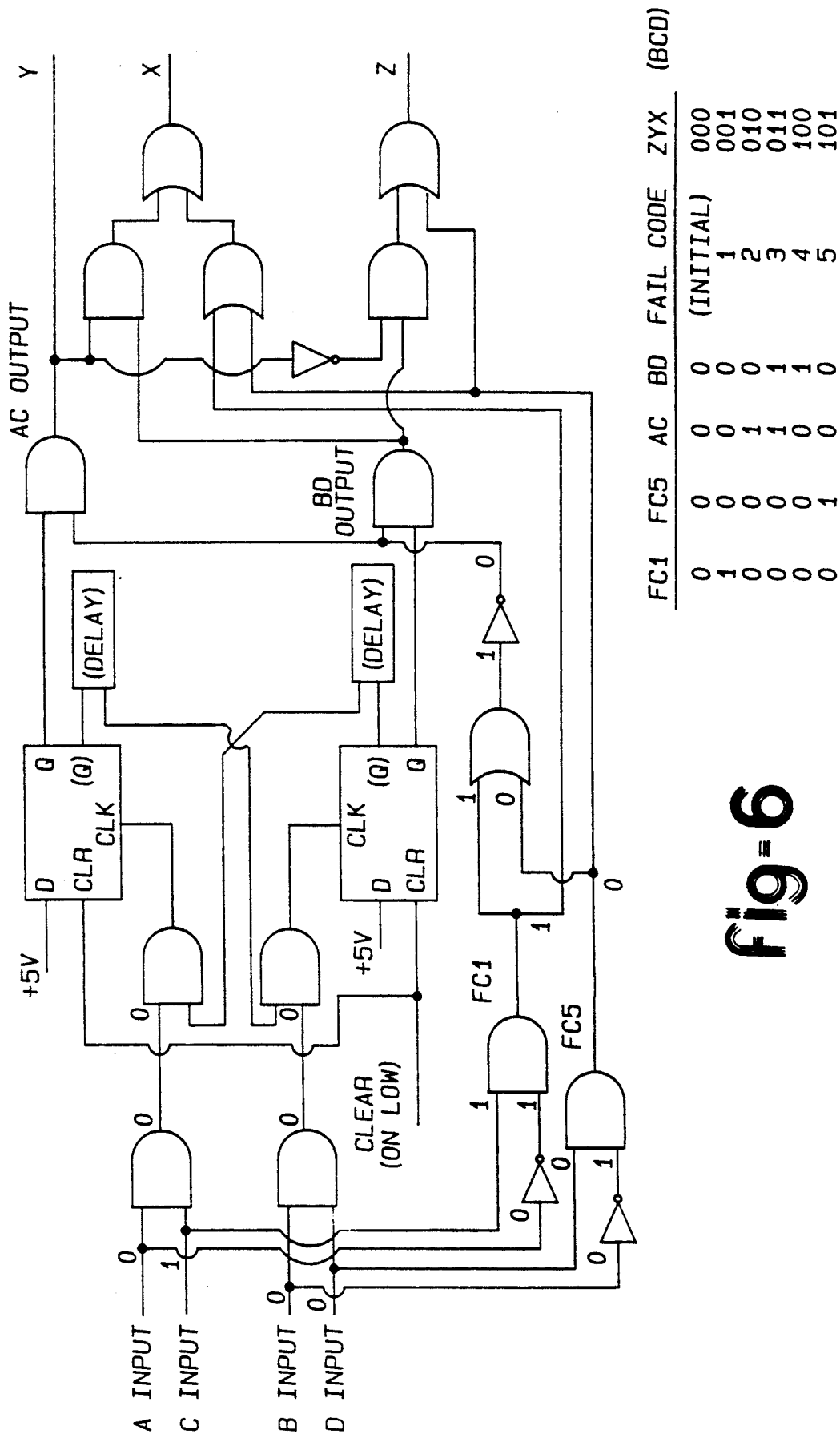
FIG. 6 is a schematic circuit diagram of the wire bond pull test failure mode detection circuit according to the present invention.

As shown in FIGS. 6-8, signals are generated corresponding to the detected voltages at references points A-D and input to respective comparators 58, 60, 62 and 64. These comparators are biased by a selected input voltage (here 2 volts) which the input signals are compared to. In the preferred embodiment, a logic 0 output signal is generated when the detected lead voltage is less than the reference voltage and a logic 1 output signal is generated when the detected lead voltage exceeds the reference value. Thus, in the initial state, the binary product of inputs A and C as well as the binary product of inputs B and D will be a logic 0. Similarly, FC1 which is the binary product of inverted input A and input C will also be 0. FC5, which is the binary product of inverted input B and input D is 0 as well. Those skilled in the art will follow the completed logic diagram of the circuit illustrated in FIGS. 6-8 to see that the binary output Z, Y, X is 000 which corresponds to the initial state.

Failure Mode 1—Lift at First Bond Foot

Referring now to FIG. 3B, a similar analysis is provided in respect of the detected voltages and the binary output. FIG. 3B illustrates a lift at the first bond foot 16, thus the detected voltage at reference points A and C is 0 and 5 volts, respectively. As in the initial state, reference hook 12 shorts the input at reference points D and B, thus the respective detected voltages are both 0. Again, corresponding signals are generated and input to respective comparators 58, 60, 62 and 64 which generate binary output signals as follows:

A=0; B=0; C=1; and D=0.

Thus, the binary product of A and C and B and D are both 0. The binary product of inverted input A and input C is 1 and the binary product of inverted input B and input D is 0. Again, the following logic of the circuit diagram shown in FIGS. 6–7, the binary output Z, Y, X is 001 which, in turn, corresponds to a lift at first bond 16.

Failure Mode 2—Broken Heel of Interconnect Wire at First Bond Foot

Referring to FIG. 3C, it is seen that in the state where interconnect wire 14 breaks at first bond 16, resistors 50 and 52 will create a voltage divider situation in cooperation with primary and secondary leads 24 and 26 of first probe 28. Those skilled in the art will recognize that the voltage divider situation results due to the equal value resistances 50 and 52. Although 10 KΩ resistors have been selected by Applicants in the preferred embodiment, it is understood that other equivalent values can be utilized while making minor changes to the circuitry, including the biasing potential of comparators 58, 60, 62 and 64 to achieve the same result.

Still referring to FIG. 3C, it is seen that the detected voltage at reference points A and C is 2.5 volts. As in the case of Failure Mode 1, the detected voltage at reference points D and B is again 0. This information is provided to corresponding comparators 58–64 which generate respective binary signals as follows:

A=1; B=0; C=1; and D=0.

As a result, the binary product of reference inputs B and D is 0 while the binary product of reference inputs A and C is 1. Likewise, FC1 and FC5 are both 0. Once the logic of the circuit is completed, the binary output of Z, Y, X is 010 which of course, corresponds to a broken heel of interconnect wire 14 at first bond foot 16.

Failure Mode 3—Center Span Failure

Referring now to FIG. 3D, it is readily seen that a break in the center span of interconnect wire 14 in combination with equal value resistors 50, 52, 54 and 56 results in dual voltage dividers such that the detected voltage at reference inputs A–D are all 2.5 volts. Comparing this information to the 2 volt reference value of comparators 58–64, generates binary output signals all having a logic value of 1. As a result, the binary product of reference inputs B and D as well as A and C are both 1. FC1 and FC5 are both 0. According to the circuit disclosed in FIGS. 6 and 7, the binary output Z, Y, X is therefore 011 which corresponds to a center span failure.

Failure Mode 4—Broken Heel at Second Bond Foot

Referring now to FIG. 3E, it is again seen that test hook 12 again creates a short across reference inputs A and C resulting in a detected voltage of 0. Similarly, equal value resistors 54 and 56, in cooperation with primary and secondary leads 30 and 32 create a voltage divider situation. As a result, the detected voltage at reference inputs D and B is 2.5 volts. Providing this information to the corresponding comparators 58, 60, 62 and 64, binary output signals are generated as follows: A=0; B=1; C=0; D=1.

As a result, the binary product of B and D is 1 and the binary product of A and C is 0. Similarly, FC1 is 0 and FC5 is 0. The resultant binary output Z, Y, X of the circuit is 100 which corresponds to a broken heel at the second bond foot.

Failure Mode 5—Lift at the Second Bond Foot

Referring now to FIG. 3F, in this final failure mode, it is again seen that test hook 12 creates a short at reference inputs A and C with a corresponding detected voltage of 0. In contrast, the lift of bond foot 18 from second support pad 22 results in a detected voltage at B of 0 and a detected voltage at reference point D of 5 volts. Providing this information to the corresponding comparators 58–64, binary output signals are provided as follows:

A=0; B=0; C=0; D=1.

As a result, the binary product of reference inputs B and D as well as A and C are both 0. FC1 equals 0 and FC5 equals 1. The binary output of the circuit Z, Y, X is 101 which corresponds to a lift at the second bond foot 18.

Referring now to FIGS. 7 and 8, attention is directed to the built-in settling time inherent in the circuit which is necessary to provide the proper balancing to detect failure mode 3, yet not be misinterpreted as failure mode 2 or 4. In the preferred embodiment, a settling time of 2.5 milliseconds has been selected and is achieved through the use of D flip-flops and internal timer circuits.

It should be understood that the detection circuit is comprised of two sections to detect failure modes 2, 3, 4 and 1, 5. In the first case (failure modes 2, 3, or 4), the lead voltages at each probe will respond simultaneously so the signals are fed to the two AND gates of the section. The signals are then sent to the clock inputs of D flip-flops which detect which signal arrived first within a given delay time set by the timer circuits (556). The time delay circuit will allow signals to arrive at the opposite flip-flop until it has "timed-out."

In the case of a heel failure (failure modes 2 or 4), the timing circuit will allow the detection of the failure and then block any further signals after the time-out period. Immediately after a center span failure (mode 3), each side of interconnect wire 14 may remain in contact with test hook 12 longer than the other side. The delay circuit thus allows the hook to clear both sides of the wire before locking in a center span failure mode.

The second section of the circuit detects wire lift failures (failure modes 1 or 5). In this case, the two lead voltages at each probe will respond independently and the signals may be fed to the NOT and AND gates which detect the wire lift failure mode. The remainder of the circuit decodes and values and outputs a binary number indicating the failure mode number.

It should be understood that each of the voltage leads of the first and second probes 28 and 34 come in contact with respective bond pads and bond foots of the wire being tested. The test hook 12 is also electrically connected to the detector circuit and comes in contact with the interconnect wire 14. The detector circuit disclosed herein monitors the voltage level of the probes. When the wire pull test is initiated, the test hook 12 begins to apply force to the interconnect wire 14 which will eventually fail. At the instant the wire fails, the probe voltages will change and the detector circuit will then identify at what point the wire failed by converting the voltages to logic values, determining which probe voltage has changed, and providing a binary digital output. It is anticipated that the circuit disclosed herein can be incorporated into an automatic wire bond pull tester to provide unattended test capability and recording.

While the best mode for carrying out the invention has been described in detail, those familiar with the art to which this invention relates will recognize various alternative designs and embodiments for practicing the invention as defined by the following claims.

We claim:

1. For use in cooperation with a wire bond pull test machine, an apparatus for electrically detecting the location of bond failure and wire breakage occurring during tensile strength testing of a wire sample having first and second bond foots affixed to respective first and second support pads, the apparatus comprising:

a first electrically conductive probe having a primary lead in electrical contact with said first support pad and a secondary lead in electrical contact with said first bond foot;

a second electrically conductive probe having a primary lead in electrical contact with said second support pad and a secondary lead in electrical contact with said second bond foot;

voltage detection means in electrical contact with said first and second probes for detecting the voltage level at each of said respective primary and secondary leads and generating respective output signals corresponding thereto; and comparator means in electrical contact with said voltage detection means for receiving and comparing each of said output signals to a selected reference value and generating a supplement output signal indicating the location of bond failure or wire breakage.

2. An apparatus as in claim 1 wherein each of said primary and secondary leads of said first and second electrically conductive probes are spring loaded and independently movable with respect to one another.

3. An apparatus as in claim 1 further including power supply means in electrical contact with each of said secondary probe leads for applying a selected electrical potential thereto.

4. For use in cooperation with a wire bond pull test machine having a grounded test hook, an apparatus for electrically detecting the location of bond failure and wire breakage occurring during tensile strength testing of a wire sample having first and second bond foots affixed to respective first and second support pads, the apparatus comprising:

a first electrically conductive probe having a primary lead in electrical contact with said first support pad and a secondary lead in electrical contact with said first bond foot;

a second electrically conductive probe having a primary lead in electrical contact with said second support pad and a secondary lead in electrical contact with said second bond foot;

power supply means in electrical contact with each of said secondary probe leads for applying a selected electrical potential thereto;

voltage detection means in electrical contact with said first and second probes for detecting the voltage level at each of said respective primary and secondary leads and generating respective output signals corresponding thereto;

comparator means in electrical contact with said voltage detecting means for receiving and comparing each of said output signals to selected reference values and generating respective first, second, third and fourth digital signals indicating whether said detected voltages exceed said selected reference values; and decoding means in electrical contact with said comparator means for receiving said digital signals and generating a binary output corresponding to said bond failure or wire breakage.

5. An apparatus as in claim 4 wherein each of said primary and secondary leads of said first and second electrically conductive probes are spring-loaded and independently movable with respect to one another.

6. An apparatus as in claim 4 wherein said decoding means comprises:

first gate means for receiving digital input signals and generating digital output signals corresponding to the binary product of said input signals;

delay means in electrical contact with said first gate means for providing a selected settling time to eliminate unwanted feedback;

second gate means in electrical contact with said first gate means and said delay means for receiving digital input signals and generating digital output signals corresponding to the binary sum of said input signals; and inverter means in electrical contact with said first and second gate means for receiving and inverting said digital output signals.

7. An apparatus as in claim 6 wherein said first gate means comprises a plurality of AND gates.

8. An apparatus as in claim 6 wherein said second gate means comprises a plurality of OR gates.

9. An apparatus as in claim 4 wherein said comparator means comprises first, second, third and fourth inverting operational amplifiers.

10. An apparatus as in claim 4 wherein said decoding means comprising:

first gate means in electrical contact with said comparator means for receiving first and second digital signals and generating a fifth digital signal corresponding to the binary product of said first and second digital signals;

second gate means in electrical contact with said comparator means for receiving said third and fourth digital signals and generating a sixth digital signal corresponding to the binary product of said third and fourth digital signals;

first inverter means in electrical contact with said comparator means for receiving and inverting said first digital signal;

second inverter means in electrical contact with said comparator means for receiving and inverting said third digital signal;

third gate means in electrical contact with said comparator means and said first inverter means for receiving said second digital signal and said inverted first digital signal and generating a seventh digital signal corresponding to the binary product of said second digital signal and said inverted first digital signal;

fourth gate means in electrical contact with said comparator means and said second inverter means for receiving said fourth digital signal and said inverted third digital signal and generating an eighth digital signal corresponding to the binary product of said fourth digital signal and said inverted third digital signal;

delay means in electrical contact with said first and second gate means for providing a selected settling time to eliminate unwanted feedback, said delay means generating ninth and tenth digital signals;

fifth gate means in electrical contact with said third and fourth gate means for receiving said seventh and eighth digital signals and generating an eleventh digital signal corresponding to the binary sum of said seventh and eighth digital signals;

third inverter means in electrical contact with said fifth gate means for receiving and inverting said eleventh electrical signal;

sixth gate means in electrical contact with said third inverter means and said delay means for receiving said tenth digital signal and said inverted eleventh digital signal and generating a twelfth digital signal corresponding to the binary product of said tenth digital signal and said inverted eleventh digital signal;

seventh gate means in electrical contact with said third inverter means and said delay means for receiving said ninth digital signal and said inverted eleventh digital signal and generating a thirteenth digital signal corresponding to the binary product of said ninth digital signal and said inverted eleventh digital signal;

eighth gate means in electrical contact with said sixth gate means and said seventh gate means for receiving said twelfth and thirteenth digital signals and generating a fourteenth digital signal corresponding to the binary product of said twelfth and thirteenth digital signals;

ninth gate means in electrical contact with said third gate means and said fourth gate means for receiving said seventh and eighth digital signals and generating a fifteenth digital signal corresponding to the binary sum of said seventh and eighth digital signals;

fourth inverter means in electrical contact with said seventh gate means for receiving and inverting said thirteenth digital signal;

tenth gate means in electrical contact with said fourth inverter means and said sixth gate means for receiving said twelfth digital signals and said inverted thirteenth digital signal and generating a sixteenth digital signal corresponding to the binary product of said twelfth and inverted thirteenth digital signals;

eleventh gate means in electrical contact with said eighth gate means and said ninth gate means for receiving said fourteenth and fifteenth digital signals and generating a seventeenth digital signal corresponding to the binary sum of said fourteenth and fifteenth digital signals; and twelfth gate means in electrical contact with said fourth gate means and said tenth gate means for receiving said eighth and sixteenth digital signals and generating a eighteenth digital signal corresponding to the binary sum of said eighth and sixteenth digital signals.

11. An apparatus as in claim 10 wherein said first, second, third, fourth, sixth, seventh, eighth and tenth gate means each comprise an AND gate.

12. An apparatus as in claim 10 wherein said fifth, ninth, eleventh and twelfth gate means each comprise an OR gate.

13. An apparatus as in claim 10 wherein said first, second, third and fourth inverter means each comprise respective first and second inverting gates.

14. For use in cooperation with a wire bond pull test machine, a method for electrically detecting the location of bond failure and wire breaking occurring during tensile strength testing of a wire sample having first and second bond foots affixed to respective first and second support pads, the method comprising the steps of:

providing a first electrically conductive probe having a primary lead in electrical contact with said first support pad and a secondary lead in electrical contact with said first bond foot;

providing a second electrically conductive probe having a primary lead in electrical contact with said second support pad and a secondary lead in electrical contact with said second bond foot;

applying a selected electrical potential to each of said secondary leads;

detecting the voltage at each of said primary and secondary leads;

generating a plurality of output signals, each of said output signals corresponding to one of said detected voltages;

comparing each of said output signals to a selected reference value;

generating a first plurality of binary output signals, each of said output signals indicating whether said detected voltage exceeds said selected reference value;

generating a second plurality of binary output signals, each of said output signals corresponding to the product of selected binary input signals;

generating a third plurality of binary output signals, each of said output signals corresponding to the sum of selected binary input signals;

generating a fourth plurality of binary output signals corresponding to said detected bond failure or wire breakage.

* * * * *